(12) United States Patent
Schirr et al.

(10) Patent No.: US 10,723,991 B2
(45) Date of Patent: Jul. 28, 2020

(54) APPARATUS AND METHOD FOR GENERATING A TOOL MOTION

(76) Inventors: Andreas Schirr, Hamburg (DE); Jens Lembke, Luebeck (DE); Andreas Graff, Hamburg (DE)

(*) Notice: Subject to any disclaimer, the term of this patent is extended or adjusted under 35 U.S.C. 154(b) by 523 days.

(21) Appl. No.: 12/972,075

(22) Filed: Dec. 17, 2010

(65) Prior Publication Data

US 2011/0212521 A1  Sep. 1, 2011

Related U.S. Application Data

(60) Provisional application No. 61/289,669, filed on Dec. 23, 2009.

(30) Foreign Application Priority Data

Dec. 23, 2009  (EP) .................................... 09015977

(51) Int. Cl.
  *C12N 15/89* (2006.01)
  *C12M 1/26* (2006.01)
  *A61M 37/00* (2006.01)

(52) U.S. Cl.
  CPC ............ *C12M 33/04* (2013.01); *C12N 15/89* (2013.01); *A61M 37/0092* (2013.01)

(58) Field of Classification Search
  CPC . C12N 15/89; A61M 37/0092; H01L 41/0536
  USPC .............................................. 435/455, 285.1
  See application file for complete search history.

(56) References Cited

U.S. PATENT DOCUMENTS

| | | | |
|---|---|---|---|
| 4,169,984 A * | 10/1979 | Parisi ..................... | A61C 17/20 310/323.18 |
| 5,229,679 A | 7/1993 | Higuchi et al. | |
| 5,877,008 A * | 3/1999 | Remenyik et al. ........ | 435/285.1 |
| 6,201,339 B1 * | 3/2001 | Tani ...................... | H01L 41/094 310/328 |

(Continued)

FOREIGN PATENT DOCUMENTS

DE  20 2009 001366 U1  4/2009
EP     2 338 972 A1  6/2011
(Continued)

OTHER PUBLICATIONS

Database WPI, Week 199623, Thomson Scientific, London, GB; AN 1996-225675 (1996).
(Continued)

*Primary Examiner* — Jonathan M Hurst
(74) *Attorney, Agent, or Firm* — Todd A. Lorenz

(57) ABSTRACT

The invention relates to an apparatus according to the present invention for generating the motion of a tool, in particular for the work on biological cell material, in particular for performing ICSI, comprises at least one actuator element, an actuated member, a motion section, at which can be arranged a tool and which is linked to the actuated member, the actuated member being elastically deformable, the actuator element being linked to the actuated member such that an actuation by the actuator element elastically deforms the actuated member by a distance, which corresponds to a length change of the actuated member, wherein said length change causes said motion of the motion section. Further, a corresponding method for generating a tool motion is provided.

17 Claims, 5 Drawing Sheets

(56) References Cited

U.S. PATENT DOCUMENTS

| | | |
|---|---|---|
| 6,251,658 B1 | 6/2001 | Henderson et al. |
| 6,661,575 B1 | 12/2003 | Yakovenko |
| 6,673,086 B1 | 1/2004 | Hofmeier et al. |
| 8,198,072 B2 * | 6/2012 | Miyawaki .............. C12M 35/00 310/317 |
| 2007/0087436 A1 | 4/2007 | Miyawaki et al. |
| 2008/0213899 A1 | 9/2008 | Olgac |
| 2009/0069712 A1 * | 3/2009 | Mulvihill et al. ............ 600/564 |
| 2009/0220387 A1 | 9/2009 | Guu et al. |

FOREIGN PATENT DOCUMENTS

| | | |
|---|---|---|
| JP | H03-166081 A | 7/1991 |
| JP | H07-38027 U | 7/1995 |
| JP | H08-290377 A | 1/1996 |
| JP | H08-52679 A | 2/1996 |
| JP | H08-86272 A | 4/1996 |
| JP | H09-219544 A | 8/1997 |
| JP | H09-278146 A | 10/1997 |
| JP | 2004-041023 A | 2/2004 |
| JP | 2005-074586 A | 3/2005 |
| JP | 2009-211029 A | 9/2009 |
| WO | WO 2000/078918 A1 | 12/2000 |
| WO | WO 2003/049908 A1 | 6/2003 |
| WO | WO 2007/004407 * 11/2007 | .............. C12M 1/26 |

OTHER PUBLICATIONS

Database WPI, Week 199618, Thomson Scientific, London, GB; AN 1996-175123 (1996).

Extended European Search Report, European Patent Office, regarding European Application No. 09015977, held in the name of Eppendorf AG, dated Jul. 28, 2010.

Extended European Search Report, European Patent Office, regarding European Application No. 10002958, held in the name of Eppendorf AG, dated Oct. 26, 2010.

Hengstenberg, R., "A Piezoelectric device to aid penetration of small nerve fibers with microelectrodes," J. Neurosci. Methods 4:249-255 (1981).

International Search Report, European Patent Office, regarding PCT Application No. PCT/EP2010/007843, held in the name of Eppendorf AG, dated Apr. 19, 2011.

U.S. Appl. No. 13/510,265 (U.S. Publication No. 2013/0013115 A1), entitled, "System and Method for Generating a Tool Motion," filed Oct. 1, 2012, of Schirr, Andreas, et al.

* cited by examiner

APPARATUS AND METHOD FOR GENERATING A TOOL MOTION

The present invention relates to an apparatus and a method for generating a tool motion, in particular for the work on soft biological cell material.

Such apparatus and methods are known from the use in biomedical applications, for example, in particular for the enucleation and nucleus transfer of cells. In the field of in-vitro-fertilization (IVF) of human or animal cells, a method is known, the so called Intracytoplasmic sperm injection (ICSI), which is an in vitro fertilization procedure in which a single sperm is injected directly into an egg cell (oocyte). The oocytes of mice or rats typically have a diameter of 100 to 120 μm. This relatively large cells allow to mechanically treat the involved biological components. The ICSI method is performed under a microscope using micromanipulation devices, comprising micromanipulators for a precise positioning, micro injectors for applying pressure or feeding small volumes in the order of few microliters, for example, and micro capillaries for guiding the flow path of small volumes and for making contact with living cells, in particular. The oocyte is stabilized by a holding capillary with the gentle suction applied by a micro injector. From the opposite side a thin, hollow glass micro capillary, with an opening diameter of typically only few (e.g. 7) μm, is used to collect a single sperm, having immobilized it by cutting its tail with the tip of the micro capillary. The micro capillary is pierced through the oolemma and into the inner part of the oocyte (cytoplasm). The sperm is then released into the oocyte. During the ICSI, the oocyte has to be penetrated by the micro capillary. Hereby, the outer protection hull of the oocyte, the zona pellucida, turns out to be resistant and requires a special apparatus for the penetration. The same is required for the biomedical method of Assisted Hatching, wherein the zona pellucida is punctually eroded from the outside, to facilitate the hatching of the developing embryo.

Such apparatus and methods are further known from the dissection of soft cell material, for example, tissue. Such a known apparatus, a microdissector, is shown in FIG. 1 of the drawings. The microdissector 1 serves for the dissection of cell tissue, e.g. for the extraction of biological components and structures from histological specimen. Due to the working principle of the microdissector 1, the base generally has U-shaped configuration. In the upper opening of the "U" a piezoelectric actuator 2 is mounted, which moves the left side piece of the "U" in relation to the right side piece. As the left side piece of the "U" is mounted displaceable on the base via the pivotable support arms 4, the tool 5, which is mounted to the motion section 5b of the base 3, can be moved along the direction of the x-axis. However, due to the pronounced U-shape, in particular the relatively large determined length of the support arms 4, the motion also shows a relatively large component in the y direction. Furthermore the "U" shaped base is especially prone to torsion around the x-axis, due to its long leverage arms in y-direction. Piezoelectric actuators usually do not expand and constrain in an optimal linear way, e.g. just in x-direction. Instead they tend to curve a bit, which in this case translates into an additional motion in y- and z-direction. Such a more-dimensional motion can be sometimes useful but is not always desired.

It is an object of the present invention to provide an improved apparatus and method for generating a tool motion, in particular for the work on soft biological cell material.

The present invention achieves said object by providing an apparatus according to claim 1 and a method according to claim 12. Preferred embodiments of the present invention are subject matter of the subclaims.

The apparatus according to the present invention for generating the motion of a tool, in particular for the work on biological cell material, comprises at least one actuator element, an actuated member, which is elastically deformable, a motion section, at which a tool can be arranged and which is linked to the actuated member, the at least one actuator element being linked to the actuated member such that an actuation by the at least one actuator element elastically deforms the actuated member by a distance, which corresponds to a length change of the actuated member, wherein said length change causes said motion of the motion section.

The apparatus and the method according to the invention are preferably adapted for their use in biological, medical, biomedical or chemical (for example biochemical) applications and the like, preferably for working on soft matter and preferably not adapted for the work on non-soft matter. Soft matter is understood to be matter like biological matter. e.g. tissue, e.g. with a Young's modulus smaller than preferably 10 GPa, 5 GPa, 1 GPa, 0.1 GPa, 0.01 GPa, or 0.001 GPa, respectively. However, the application of the apparatus and the method according to the invention with regard to non-soft matter, in particular for matter with Young's modulus larger than 10 GPa, is also possible. The apparatus and the method according to the invention are preferably used and adapted to be used for IVF, ICSI, Assisted Hatching, Enucleation, Nucleus transfers, Micro chirurgery, Patch Clamp and other biological and medical fields, in particular adapted to be used for working on cells from humans, animals, e.g. mice, rats or bovines, in particular on oocytes, or are adapted to be used for multiple of such applications, respectively. The apparatus is further preferably adapted for performing the Dissection of cell material, e.g. the single cell dissection from paraffin sections, the dissection of areas from histological sections and/or the Separation from stem cell aggregates from 3D-cell cultures. However, the apparatus and/or the method can be used also for other applications, in particular to non-biomedical applications, which in particular require a motion with amplitudes in the nanometer to micrometer range or other ranges and general for those applications, which can benefit from the advantages and features of the apparatus and/or the method according to the present invention.

The motion of the motion section of the apparatus according to the invention is realized by means of an actuated member, which is actuated by at least one actuator element and which itself actuates the motion section, which is linked to the actuated member. Preferably, one actuation action by the at least one actuator element elastically deforms the actuated member by a distance, which substantially equals to the effected one length change of the actuated member. Preferably, the actuation action of the at least one actuator element leads to a net length change of the actuated member. Preferably, a second length change of the actuated member is caused by substantially the first length change of the at least one actuator element, which performs one actuation action. Said first length change and said second length change preferably take place substantially at the same time. Preferably, there is substantially no phase shift between the motion of the actuated member and the motion of the at least one actuator element. Preferably, the value of the second length change (v_am) and the value of the first length change (v_ae) are the same. This configuration offers the advantage that a preferably direct interaction between the action of an actuator element and the (re-)action of the actuated member is achieved, which allows a more precise control of the motion of the motion section and enables the realization of displacements of the motion section with a controlled number of displacements, e.g. 1, 2, 3, 4, 5, or more definite displacements instead of performing an oscillation motion with an undefined number of oscillations. Preferably, the ratio v_am/v_ae fulfils one of the following conditions, respectively: v_am/v_ae=1; |v_am/v_ae−1|<0.5 or 0.2 or 0.1 or 0.01. Preferably, said net length change has the value v_am.

The apparatus is preferably configured such that a straight line in parallel to the direction of an at least partially linear motion of the motion section (actuated by the actuated member), which runs through the motion section or through the length of an elongated tool, which is mounted at the motion section, does not run through the actuator element or through a part of the actuator element. With such a configuration, the impacts acting from outside on the motion section or on the tool mounted to the motion section do not directly act along a straight force-transferring line on the actuator element. Rather, said impacts and other mechanical loads are at least partially or (almost) completely absorbed by the actuated member.

Most preferred, the apparatus is configured such that a force, which is exerted on the motion section or on a tool, which is mounted at the motion section, in particular, from outside the apparatus, is transferred to the actuated member, substantially, and is further transferred from the actuated member towards a connecting section, substantially, which is preferably provided at the actuated member, and is preferably further transferable via said connecting section to a holder device, which preferably is adapted to hold the apparatus and which is absorbing the force, which was exerted from outside, (almost) completely or at least partially. Therefore, the motion section, the actuated member and the connecting section, and preferably also a potential holder device, are preferably connected in series, forming a direct force transferring chain.

Moreover, the at least one actuator element is preferably mounted at the actuated member such that a force, which is exerted on the motion section or on a tool, which is mounted at the motion section, in particular, from outside the apparatus, is acting on the actuator element by a minimal fraction, only, e.g. a fraction of smaller than preferably 0.001, 0.01, 0.1 or 0.5. Rather, said force is mainly transferred and further distributed by the actuated member, preferably towards a connecting section at the actuated member, and is preferably further distributable to a holder device, which can be provided to hold the apparatus at said connecting section.

Preferably, a force acting on the motion section is distributed between the actuator element (ae) and the actuated member (am) in a ratio force_on_ae/force_on_am, said ratio being preferably smaller than 0.5; 0.25; 0.2; 0.1; 0.5; 0.01; 0.005; 0.001; respectively. This can be achieved, in particular, if the resistance, which counteracts an impact force, which acts on the motion section, is mainly based on the resistance of the actuated member and is less based on the resistance of the actuator element. For implementing this, an arrangement of the actuated member and the at least on actuator element is preferred, which promotes the distribution of said force in a larger fraction on the actuated member and in a lower fraction on the actuator element(s), which is realized by several embodiments of the apparatus according to the present invention, in particular.

Further, the actuated member will provide a larger amount of resistance, if the capability of the same to deform under the application of a deformation energy (e.g., upon an impact force) is relatively low, e.g. compared to the corresponding capability of the actuator element, and is relatively high for the actuator element. Thus, the Young's modulus of the material of the actuated member (Y_am) is preferably relatively high and the Young's modulus of the material of the actuator element(s) (Y_ae) is preferably relatively low. Preferably. Y_ae is lower than the Y_am by a factor of at least 0.9, 0.85, 0.75, 0.5, 0.25, 0.1 or 0.05. For example, it is preferred that 0.85<Y_ae/Y_am<0.90, 0.5<Y_ae/Y_am<0.80 or 0.1<Y_ae/Y_am<0.5.

These configurations offer the advantage that the apparatus is more robust than other apparatus, where the motion section is connected in a straight force-transferring chain directly to the actuator, e.g. a piezoelectric element, which may be damaged upon an unintended impact of the tool to a glass substrate, long-term stress or other mechanical stress, which acts undamped via said line of components on the actuator. The present invention utilizes the actuated element, which buffer impacts, offers a higher structural stability and robustness and makes the method according to the invention more reliable. In such a configuration, the actuated member can be seen to be the "backbone" of the apparatus, which is moved by the actuator element(s), which are preferably mounted in parallel to the actuated member ("backbone"), thus forming the "muscle".

Further, the linkage of the actuator element(s) relative to the actuated member according to the invention allows to use lighter and smaller components, providing a lower total mass of the system, which allows faster actuation changes, and higher oscillation frequencies for the case of an oscillating motion. Moreover, the actuator element(s) can be arranged closer to the motion section, to make the force transfer to a possible tool (capillary etc.) more effective. In particular, preferably avoiding the known U-shaped arrangement leads to a better torsional stiffness of the apparatus. This is of crucial importance for the preferred case of using piezoelectric actuators. Piezoelectric actuators usually do not expand and constrain in an optimal linear way, e.g. just in x-direction. Instead they additionally tend to curve a bit, which translates into an unintended motion of the motion section in x- and/or y-direction, if not prevented by the actuated member. The "U" shape is especially prone to torsion around the x-axis, due to its long leverage arms in y-direction.

Linkage of a first element to a second element in the context of the invention preferably means a kinematical coupling of both parts, preferably where the motion of the first element results in a motion of the second element. Linkage and "to be linked" can mean that both parts are permanently or non-permanently fixed to each other in all dimensions or at least one or two dimensions, e.g. by integrally forming both parts or by a connection from at least one of the types force-closure, form-closure or adhesive bond. Linkage of a first part and a second part further includes the case that the first part is linked to the second part via a third part or further parts, wherein for example the first part is linked to the third part and the third part is linked to the second part. Here, for example the first part can be the actuator element, the second part can be the actuated element and the third part can be one or more connecting means. For the apparatus and the method according to the invention, it is preferred that linkage of the components is such that a play between the components is avoided. In particular, no floating bearing has mandatory to be utilized for the apparatus. This makes the design of the apparatus less costly and improves the accuracy of the generated motion and the capability of the apparatus.

The motion section is preferably integrally built with another part of the apparatus, e.g. integrally built with the actuated member. The actuated member preferably extends along a central axis, and the motion section preferably is arranged at the actuated member such that said axis extends through said motion section. In particular, the motion section is the section of the apparatus, which is adapted for mounting a tool, preferably.

The motion section is preferably adapted to permanently or removably carry or connect or hold a further element, in particular a tool, e.g. a microdissector needle or a capillary, said tool preferably made from metal, glass or plastic.

Preferably, a mounting head for removably mounting a tool is firmly connected or connectable to the motion section, such that the motion, which is supplied by the apparatus, in particular by the actuated member, is preferably completely, but preferably at least partially, transferred to the tool in order to move the tool. The mounting head may comprise connecting means for connecting an element, e.g. the tool, to the mounting head. The connecting means may comprise a thread, a means for latching, a magnet and/or the like. The mounting head can be formed integrally with another part of the apparatus, e.g. the actuated member or a carrier. A second mounting head is preferably provided to be removably connected by second connecting means with the first mounting head to allow using different second mounting heads, which are respectively adapted to hold a specific type of element, e.g. tool, for example the type depending on the outer diameter of a capillary or needle.

The mounting head can be adapted to form at least one channel, such that a fluid may flow through the mounting head. This can be useful to apply pressure or low-pressure, if for example a capillary is used as a tool, to use said pressure changes and a controlled pressure to work on the target material, e.g. the cell. The use of channels is preferred for the use of the apparatus in combination with a microinjector or for patch clamp applications, where an electric contact is made via the conductive electrolyte in the channel, or for other applications, where channels are useful. Further, the optional second mounting head can be adapted to form a channel, such that a fluid may flow through the mounting head. If required, sealing means, e.g. O-rings from plastic, are provided to seal the interior of said channel relative to the exterior, in particular to seal the channel at the junction sites, where two channel parts are connected.

The actuated member preferably is the part of the apparatus which can be actuated by the actuator element and is the part of the apparatus, which serves as the actuator which moves the motion section.

The actuated member preferably is a base part or part of a base part, which preferably carries other components of the apparatus. For example, the base part can be the carrier of the at least one actuator element and/or of any linking means, which link the actuator element(s) to the actuated member at its first and second position. Preferably, the actuated member is an integrally formed part. However, it is also possible and preferred that the actuated member comprises at least two parts or more, which are linked to each other, preferably fixed to each other in all three dimensions.

The actuated member preferably provides at least one channel, such that a fluid may flow through the actuated member. Also here, this can be useful to apply pressure or low-pressure, if for example a capillary is used as a tool, to use said pressure changes and/or a controlled pressure to work on the target material, e.g. the cell. If required, sealing means, e.g. O-rings from plastic, are provided to seal the interior of said channel relative to the exterior, in particular to seal the channel at the junction site. The channel can be adapted to be filled with gas, liquids, in particular to be filled with cell plasma, culture medium, water, solution, or with mercury. Fluorinert™ or silicon oil. However, providing a channel or a filled channel is not mandatory but optional for the apparatus and the method according to the invention.

The actuated member may be a bar part or a tubular part, which preferably extends along a (virtual) axis and which preferably is at least in part built symmetrically in relation to said axis. Preferably, the actuated element is an elongated device, where the length is larger than the height or the depth, respectively, and a virtual axis runs through the actuated member, in parallel to its length; further the actuator elements are arranged to act along a second virtual axis, substantially, to mainly generate a linear motion of the actuator element(s) in parallel to said second axis; the actuated member and the at least one actuator element are preferably arranged such that the first axis and the second axis are parallel or coaxial. Further preferred, the net force vector, which results from the motion of said actuator element(s) in parallel to said second axis, matches with the center of area or centroid of a cross section of the actuated member, said cross section taken preferably perpendicular to said first axis, which preferably applies for all possible cross sections or at least the majority of cross sections of the actuated member. This offers the advantage, that the actuated member will just be elongated but substantially not bended, which results in small cutting or drilling width of the tool. Preferably, the actuated member is, or comprises, a hollow-cylinder shaped part or a tube, forming a channel. A tube or a channel offers the advantage that pressure or under-pressure can be applied to an appropriate tool, e.g. a capillary, to mechanically treat the target soft material of the sample, e.g. the cell, by pressure or by injecting volumes of injection material, e.g. a sperm, to the target material (e.g. a cell), or to remove volumes of the target soft material from the sample. It is preferred that said tube or channel is filled with a fluid, which preferably is a gas, e.g. air, a liquid, e.g. Fluorinert®, or mercury.

The actuated member preferably comprises third connecting means, which are preferably built integrally with the actuated member, for connecting or linking other parts, e.g. the at least one actuator element, to the actuated member. A position, at which such a third connecting means is preferably linked to the actuated member, is said first and/or second position, at which the at least one actuator member is preferably linked to the actuated member.

Said third connecting means may comprise at least one projection or at least one recess, which preferably is arranged circumferentially at the actuated member around the axis, along which the actuated member extends. Preferably, the third connecting means comprises a projection, a recess or a step in the outer surface of the actuated member, which preferably respectively provides an engagement site for the engagement of complementary formed connecting means.

The actuated member preferably provides a first position and a second position, wherein the actuated member preferably extends along, preferably extends in parallel to a distance between said first position and said second position and preferably extends in parallel to a straight distance, defining an axis, between said first position and said second position. Between said first and said second position, the actuated member is preferably formed such that an increase or decrease of said distance preferably expands or compresses the material of the actuated member along said distance, preferably without bending it or preferably by additionally bending it. The straight distance between said first and said second position is preferably between 5 and 100 mm, preferably between 5 and 50 mm, preferably between 10 and 50 mm, preferably between 10 and 30 mm, preferably as well in a first status, where the actuated member is not elastically deformed as well as in a second status, where the actuated member is elastically deformed. Preferably, said distance is used only for expansion of the actuated member to expand the actuated member along the length of said distance. Having said elastical deformation applied directly to the actuated member, which preferably forms the backbone of the apparatus, offers the advantage that the dimensioning of the apparatus can be kept smaller if compared for example with the known apparatus with U-shaped base. Further, the provision of an internal expansion distance in the apparatus offers the advantage that the operation is more independent from the suspension of the apparatus, which may be connected to other micromanipulators with linear motors etc., thus allowing more flexibility for the application of the apparatus.

The actuated member preferably is non-deformed in its first status, deformed in its second status and less deformed in a third status. In the third status, the actuated member preferably is less deformed than in the second status by a factor of at least 10^2, 10^3 or 10^4 or different. In the third status, the at least one actuator element preferably is hold under elastic mechanical stress, preferably under compression, by means of the actuated member. The compression, preferably a bias compression, is preferably chosen such that at no time of the operation of the apparatus the actuator element gets under tensile stress. Said compression, for example, can result in a bias force of 1025 N, if the fastening torque of the counter support, which compresses the actuator element, is 500 Nmm, in an idle state of the actuator element. This can be achieved by the connecting means, e.g. comprising a thread, which preferably fix the actuator element to the actuated member, which preferably carries said components. The benefit of such a bias stress is that a play between the actuator element and the actuated member can be avoided in all of its status. Therefore, the force of the actuator element can immediately and directly be transferred to the actuated member. If the actuator element comprises a piezoelectric element, the bias compression in particular leads to an increased load capability of the piezo element. The ability to work under pressure for piezo elements is much higher than to work under tension, sometimes 10 to 20 times higher. Besides the risk of a brittle failure, there is a risk of depolarising the piezo elements, when it is under tensile stress with the wrong voltage. When driving piezo elements under a permanent (bias) compression, the mechanical load capability can be increased compared to a system with mixed tensile/compressive status and higher frequencies of alternate supply power can be applied. A main advantage of providing a bias force is that a faster forward and backward motion of the motion section can be achieved. The motion section can be returned by a fast voltage shift without having the risk of a depolarisation of the actuator element (e.g. Piezo element), which can arise in the case of a tensional load.

The actuated member is preferably made from an elastic material or at least partly made from an elastic material or comprises sections made from an elastic material. Further, the actuated member preferably comprises sections of different elasticity. Said elastic material has a Young's Modulus of preferably larger than 0.2 kN/mm², preferably larger than 100 kN/mm², preferably larger than 200 kN/mm² and preferably between 180 to 240 kN/mm². Preferably, said elastic material is or comprises steel, ceramics or glass. Steel or other material with Young's Modulus of preferably larger than 180 kN/mm² offer the advantage that stable structures, in particular stable actuated sections can be designed. This allows in particular to construct more robust and durable apparatus and to provide more reliable methods for generating a motion. On the other hand, such materials are appropriate to be compressed or expanded due to their elasticity, preferably be means of an actuator element, which comprises conventional piezoelectric elements as actuator members or other piezoelectric elements, e.g. such strong piezoelectric elements, which are e.g. applied in the car industry where they are used for fuel injectors, which can be utilized for the present invention. Preferably, the actuated member is used as electrical conductor and preferably is used as electric circuit component of the apparatus.

The length change of the actuated member in relation to any direction, which is induced by the actuation of the at least one actuator element, preferably corresponds to the difference of straight distances between said first position and said second position, when they are respectively measured in the deformed second status and the non-deformed first status of the actuated member. By definition, for an expanded actuated member, the length change has a positive sign and for a compressed actuated member, the length change has a negative sign in relation to said direction. The length change of the actuated member preferably is taken of the group of ranges of length changes, comprising 0.5 to 2.0 µm, 0.5 to 1.0 µm, 0.1 to 0.5 µm, 0.05 to 0.5 µm, 0.01 to 0.5 µm, 0.01 to 1.8 µm or different.

Said amplitudes are preferably realized by providing an actuator element with at least one piezo element, and driving said actuator element in a Voltage regime of preferably 200V to 425V, 200V to 600V, or 100V to 300V, respectively. Applying to said actuator element a respective voltage, an amplitude can be realized, wherein no bias compression is applied in this case, as described exemplarily by the following example reference list (voltage [V]; amplitude [µm]): (700; 1.1032), (600; 0.9456); (425; 0.6698), (200; 0.3152), (300; 0.4728), (100; 0.1576). Under a bias compression, the amplitudes can be expected to be slightly smaller, e.g. smaller by less than 5.0, 1.0 or 0.01%.

The maximum length change depends on the length of the actuated section or in particular on said straight distance, and on the strength of the at least one actuator elements which are employed. For a given force, elastic material with higher Young's Modulus will provide a lower length change.

The motion section is preferably linked to the actuated section such that the length change of the actuated element in a defined direction results in the motion of the motion section by an amplitude, which corresponds (preferably equals) to said length change. An amplitude of for example 50 to 250 nm can be used for ICSI, which is e.g. performed on bovine oocytes, in particular for penetrating the zona pellucida with a glass capillary having a few µm (e.g. 5-8) diameter opening. Steel or other material with Young's Modulus of preferably larger than 180 kN/mm² can provide such appropriate amplitudes, which allow to precisely work on biological cell material or on other structures.

Said elastic material preferably is homogeneous, preferably seen on a macroscopic scale in the order of 1 or 10 µm, or has at least homogeneous sections. Further it is preferred that said elastic material is not homogenous or comprises at least inhomogeneous sections. For example the material can have a structure, e.g. a grain size in the micrometer regime as the typical structure variable or a structure with structure values larger than a micrometer or millimeter. The elastic material can be made from a solid material, which can have hollow sections filled with gas of any pressure, said hollow sections preferably being pores or openings or the like.

The optional bending of the actuated member, which extends e.g. along the x-direction, by a force acting in x-direction can cause a change of the position of the motion section in x-direction. However, for the present invention it is preferred that the length change of the actuated member due to its elastic deformation upon actuation by the actuator member in x-direction is preferably the dominant effect, which shifts the motion section in x-direction, wherein the bending is preferably negligible. This is preferred in particular for the preferred case of a desired linear motion of the motion section. However, bending of the actuated member may also be intended to a certain amount, in particular to generate a motion in more than one direction, for example, at least partially also in x-, y- and/or z-direction. If a linear motion of the motion section is desired, it is preferred that the at least one actuator element is linked to the actuated member such that (substantially) no bending of the actuated member upon actuation by the actuator member occurs in said direction. If a linear motion of the motion section is intended, it is preferred that said bending is preferably negligible. Negligible means tolerable for achieving the desired technical aims of the application of the apparatus, e.g. for performing ICSI. Preferably, a linear motion provides a ratio R of the maximal amplitude $A\_y$ ($A\_z$) of the motion section or the distal tip of a tool, elongated with its proximal end to the motion section, in y-direction (and/or z-direction, respectively) in comparison with the maximal amplitude $A\_x$ in the preferred x-direction, with $R=A\_y/A\_x$ and/or $R=A\_z/A\_x$ being respectively preferably smaller than 0.5, 0.2, 0.1, 0.05, 0.01, 0.005, 0.001, 0.0005, 0.0001, more preferably 0.00005, 0.00001, 0.000005, 0.000001, 0.0000005, 0.0000001.

Further it is preferred that at least one actuator element is linked to the actuated member such that the bending of the actuated member upon actuation by the actuator element occurs with a limited amount in the direction of the motion, said direction being preferably the direction of the length change of the actuated member due to its elastic deformation upon actuation by the actuator member. A limited amount means that the first fraction, by which said bending of the actuated member shifts the motion section in the desired linear direction is small to the second fraction, which is due to the length change of the elastic deformed actuated member in said direction. Preferably, the quotient of the first fraction divided by the second fraction is smaller than 2 or smaller than 1, and respectively preferably smaller than any of the values 0.5, 0.1, 0.01 or 0.001.

At said first or second position, the at least one actuator element is preferably linked to the actuated member such that the actuated member undergoes said length change upon actuation by the actuator element. The first position can comprise or can be a point or a contact area or several points or contact areas, where an element, which transfers the force generated by the actuator element, e.g. the actuator element itself, contacts the actuated member or is linked to the actuated member, in particular to transfer a force generated by the actuator element to the actuated member. Preferably at least a third position is provided on the actuated member, at which an actuator element is linked to the actuated member.

Preferably, the actuation of an actuator element, which is linked to the actuated member, causes a length change of the actuated member along a linear distance between said first position and said second position. Preferably, the actuated member is adapted to be expanded between said first position and said second position by the length of a first length change. Further preferred, the actuated member is adapted to be compressed between said first position and said second position by the length of a second length change. Further preferred, the actuated member is adapted to be expanded between said first position and said second position by the length of a first length change and at the same time is adapted to be compressed between a third position and fourth position by the length of a second length change. Such an adaptation can be realized by configuring the actuated member at said positions to provide counter supports (e.g. projections, recesses, openings, steps) for the linkage of the at least one actuator element to said positions.

At least one actuator element is provided. Preferably multiple, e.g. two, three, four, five six or more actuator elements are provided. Each actuator element preferably comprises at least one, preferably multiple, e.g. two, three, four, five, six or even much more, like several tens or hundreds of actuator members. Preferably at least two or three actuator elements are provided, which are arranged around the actuated member to allow the actuation of the actuated member in x-, y- and z-direction of a coordinate system.

An actuator element or actuator member can be a piezoelectric element, e.g. a piezoelectric ceramics, e.g. soft- or hard-ceramics, e.g. BaTiO3, PbTiO3, Pb[ZrxTi1-x]O3 (0<x<1; PZT), KNbO3, LiNbO3, LiTaO3, Na2WO3, Ba2NaNb5O5, Pb2KNb5O15, PMN or the like.

Preferably, an actuator element or an actuator member has a ring-shaped structure, preferably a symmetrical circular-ring structure, such that it is arrangeable around the body of a cylindrically shaped actuated member. Preferably, at least one actuator element and/or at least one actuator member (e.g. a piezoelectric foil) are stacked together to form one actuating device. The actuator elements and/or the actuator members are preferably arranged in a sequence with respect to at least one direction, e.g. the x-direction. Strong piezoelectric elements are preferred, which are e.g. applied in the car industry where they are used for fuel injectors and which can be utilized for the present invention (e.g., based on PbTiO3, Pb[ZrxTi1-x]O3 (0<x<1; PZT)). Stacked Piezoelectric elements are preferred, comprising a stack of some tens to hundreds of individually connected piezo elements, e.g. piezo foils. Preferably, the actuator elements and/or the actuator elements are connected in parallel. This allows to keep the supply voltage relatively low, preferably under 600 V and more preferably under 500 V. Further, the achieved amplitudes of motion are as high as e.g. 0.5 to 1.8 µm and the control electronics are easier and cheaper to realize.

Preferably, the at least one actuator elements is/are arranged such around an axis through the actuated member, that the force vector resulting from the equal actuation of all actuator elements points in the direction of said axis. This is e.g. the case for circular shaped ring-piezo elements, which are arranged around a cylindrical shaped actuated member. This offers the advantage of a linear actuation of the actuated member and motion of the linked motion section in one well defined direction, e.g. the x-direction, which is desired for many applications, e.g. ICSI. Preferably, the at least one actuator element and connecting means, which link the actuator element to the actuated member, are arranged such that the force of the actuator element is transferred axial to the actuated member. This means that under equal control of all actuator element, their net force is acting on the center of the cross section of the actuated member. This offers the optional advantage that a bending of the actuated member is avoided. Thereby, the deflection of an optionally connected tool is reduced such that the section width or the bore diameter is reduced, because preferably only a linear motion is reached. However, it is possible and preferred that for certain applications a bending of the actuated member is allowed by differently controlling the at least one (e.g. two or three) actuator element, to achieve a more dimensional motion.

Preferably, the apparatus comprises connecting means for connecting the apparatus to a second apparatus, which can be a micromanipulator or a suspension device. Preferably, the actuated member is provided with a connecting section, which can be the part of the actuated member which is arranged opposite to the motion section, such that the actuator element/s is/are arranged between the motion section and the connecting section, but however, preferably in parallel to the actuated member. Further, it is also possible and preferred to provide a housing for the at least one actuator element, wherein then said connecting means can be arranged to the housing. Preferably, an inert mass element is provided on the apparatus, which is preferably arranged in a force transfer chain between the at least one actuator element and said connecting means, which connect the apparatus to other apparatus. Said inert mass element preferably is made from steel or other material. The function of the inert mass element in this case is to distribute the forces resulting from the actuator element in favour of the propulsion of the motion section, which preferably is the front part of the apparatus and to reduce the propulsion of the connecting means (or the optionally connected other apparatus, e.g. suspension device), which are preferably forming the back part of the apparatus. This follows the concept of Newton's third law "actio=reactio", which means that higher masses are accelerated less than the connected lower masses, resulting in a larger displacement of the lighter mass (the motion section) compared to the displacement of the larger mass (the inert mass element and the optional connected further apparatus). Thus, the generation of the motion is more efficient and the junction of the apparatus to preferably connected further apparatus as well as the further apparatus is less stressed.

Preferably, a control device is provided for the apparatus, which controls the actuation by the at least one actuator element. The control device preferably comprises electric circuitry, in particular power circuitry for controlling the supply power of the actuator element. Such circuitry preferably comprises an insulated-gate bipolar transistor (IGBT). The high voltage, which is supplied by a supply voltage generating means, preferably is distributed to the piezoelectric elements with the desired amplitude and frequency by means of an IGBT. The control device preferably comprises a microcontroller, preferably a microprocessor and preferably data storage devices, e.g. RAM. ROM or EEPROM or the like. The control device preferably is adapted to be programmable by the user of the apparatus to preferably implement predetermined motion programs, according to which a motion is generated in a desired sequence, frequency, pulse number, amplitude and the like, to improve the reproducibility of the work with the apparatus. The control device preferably is externally arranged, in particular mounted externally, from the apparatus according to the present invention and preferably connected to the apparatus via cable. However, it is also possible and preferred that the control device is linked or mounted to the apparatus.

Preferably, the apparatus comprises input means to receive signals and/or output means to send signals. The input means can comprise buttons or a control panel or the like for the user control of the apparatus. The input means can also comprise a data interface to remote control the control device by another device, e.g. a workstation or PC, for automization of the work with the apparatus. In particular, a foot switch may be provided, preferably as one of said input devices, to allow the user to take control by his feet. The foot switch may be connected to the apparatus or to an external control device. The output means may comprise visual and/or acoustical means, e.g. loudspeaker or displays or LEDs, wherein the control device is adapted to signal information on the status of the control device or the apparatus to the user. The output means can further comprise a data interface to send information to another data processing device, e.g. to a workstation or PC. Also the apparatus can comprise a control device and/or input means and/or output means, in particular a data interface, to provide information on its status and the status of the actuator elements, e.g. the piezoelectric elements. This allows to monitor the operation and the capability of the apparatus.

The control device is preferably adapted to control the actuation of the at least one actuator element. Preferably, the control device is adapted to let the at least one actuator element perform a number of actuation actions, which can be chosen by a user or can be chosen automatically, said number being preferably 1, 2, 3, 4, 5, or larger. Preferably, the control device is adapted to supply all actuator elements with the same power.

However, it is also preferred that the control device is adapted to supply different actuator elements or actuator members with different power, preferably according to a predetermined program, which preferably is stored in a data storage of the control device. Preferably, the control device is adapted to control the motion of the motion section. Preferably, the control device is adapted to generate single pulses or single impacts or a sequence of propulsions of the motion section with a predetermined or user definable number of pulses, oscillatory motions or motion patterns with different motion amplitudes, frequencies, delay times etc.

The method according to the present invention for generating the motion of a motion section of an actuator apparatus, in particular for the work on biological cell material, wherein the actuator apparatus further comprises at least one actuator element, an elastically deformable actuated member, to which the actuator element is/are linked, and a motion section linked to said actuated element, comprises the following steps: —actuating said actuated member by elastically deforming it, e.g. expanding and/or compressing it, by means of said actuator element to induce a length change of the actuated member; —generating the motion of the motion section by said length change. Further preferred configurations and advantages of the method according to the invention can be derived from the corresponding description of the apparatus according to the invention and its preferred embodiments.

Moreover, further advantages, features and applications of the present invention can be derived from the following embodiments of the apparatus and the method according to the present invention with reference to the drawings. In the following, equal reference signs substantially describe equal devices.

FIG. 1 shows a prior art apparatus, as already described above.

The embodiments of the apparatus according to the present invention relate to a "cell driller", which is the apparatus adapted to drill holes into the membranes or hulls of biological cells, as required for example for performing ICSI. The term "driller" does not mandatory imply a rotational motion of a tool, which can be connected to the driller, but may imply rotational motion.

Figure 1:
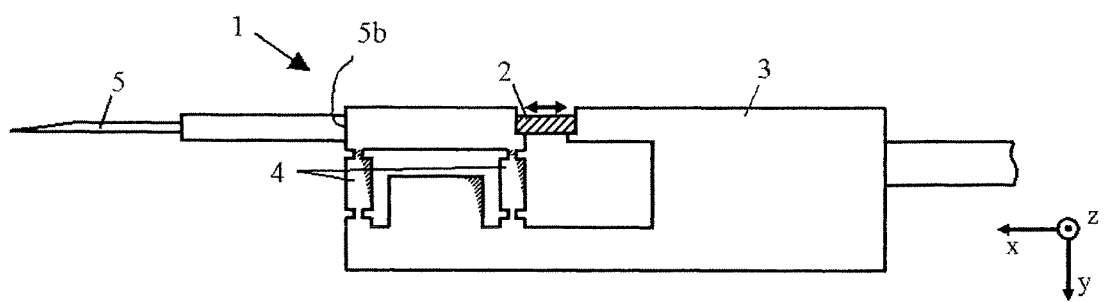
FIG. 1 shows the side view of a prior art apparatus, comprising a U-shaped base.
Figure 2:
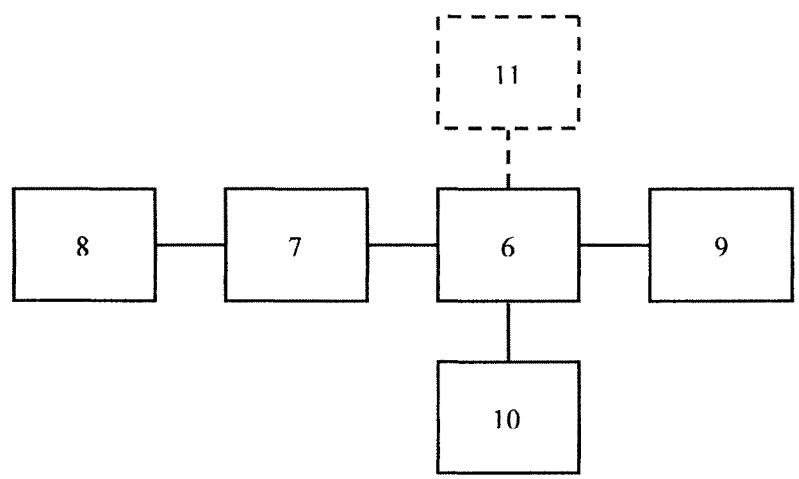
FIG. 2 shows a block diagram of a system with some functional components comprising any embodiment of the apparatus according to the present invention, which is operated according to any preferred configuration of the method according to the invention.

FIG. 2 shows a block diagram of a system with some functional components comprising any embodiment of the apparatus according to the present invention, which is operated according to any preferred configuration of the method according to the invention. The cell driller 6 is preferably used for the overall system (6; 7; 8; 9; 10; 11). The cell driller is suspended and hold by a micromanipulator 7, e.g. the Eppendorf TransferMan NK 2™. The micromanipulator 7 is mounted to an inverted microscope 8, e.g. the Nikon Eclipse Ti™.

The cell driller 6 is controlled via the external control device 9. The latter comprises a control panel and two foot switches connected to it. Alternatively, a hand switch may be used with at least two switches. The operation of the first foot switch (channel 1) triggers the start of a pulse sequence, where the tool of the cell driller 6 is linear moved forth and back according to parameters which are appropriate to penetrate the zona pellucida (zona) of an oocyte. The second foot switch (channel 2) triggers a pulse sequence appropriate to penetrate the oolemma of an oocyte. The set of parameters for both channels is determined according to respectively three single parameters: the amplitude (a) of the impulse of the tool, the number (n) of impulses in one sequence and the frequency (f) or delay time which define the temporal sequence of the impulses.

For penetrating the zona or the oolemma, the following sets of parameters are useful:
Zona:
a=preferably 0.20 to 0.95 µm, preferably 0.20 to 0.67 µm;
n=preferably 1 to 70, preferably 1 to 10;
f=preferably 1 to 40 Hz, preferably 1 to 10 Hz.
Oolemma:
a=preferably 0.12 to 0.5 µm;
n=preferably 1 to 20, preferably 1 to 5;
f=preferably 1 to 40 Hz, preferably 1 to 10 Hz.

The optimal choice of parameters depends on the type of cell, which has to be penetrated. It further depends on the capillary, which is used as a tool, and its potential filling material, which can be Fluorinert™ FC-77 or mercury. Therefore, the optimal parameters can be different from the ranges of the parameters described here. Preferably, the apparatus, i.e. the cell driller 6, is adapted to tolerate other parameters. For example, it can be possible to several times start a sequence of impulses to succeed in penetrating a specific membrane.

In addition to the cell driller function, the embodiment of the cell driller 6 described here also offers a second function and can be used as microdissector to dissect cell membranes or tissue. If the dissection mode is started via the control panel, the parameter n is preferably not selectable. Instead, the dissection tool is preferably controlled by operating the foot switch until the switch is released. It is possible to perform a norm frequency dissection with f=0 to 1000 Hz or a high frequency dissection with f=20 to 40 kHz.

Moreover, the apparatus according to the invention, in particular the cell driller 6, and/or the control device, in particular the control device 9, is/are adapted to provide a clean function, which aims to clean the tool from adhering material, e.g. cell material. The clean function can preferably be started by the control panel or by "double clicking" a foot pedal. The cleaning method provides a sequence of impulses, which is appropriate to shake off cell material at clean-frequencies, preferably between 2 to 10000 Hz, 10 to 2000 Hz, 100 to 2000 Hz, 800 to 1200 Hz, 950 to 1050 Hz or different frequencies.

If the cell driller 6 is used for the injection of material into a cell (e.g. ICSI), the apparatus requires besides the interfaces to the control device 9 and to the micromanipulator 7 also a third interface to the microinjector 11, e.g. the Eppendorf CellTram Oil™. The microinjector 11 doses smallest volumes of liquid, e.g. 100 to 1000 µm³ or different, to the capillary, in particular the volume occupied by a single human sperm of about 380 µm³ which is moved by the cell driller 6. If instead of a capillary a microelectrode is used as a tool, then the microelectrode has to be provided by an appropriate control device (11). If the cell driller 6 is used for the micro dissection of a tissue sample 10, then the microinjector 11 or a controller for a microelectrode can be omitted or disconnected.

Figure 3:
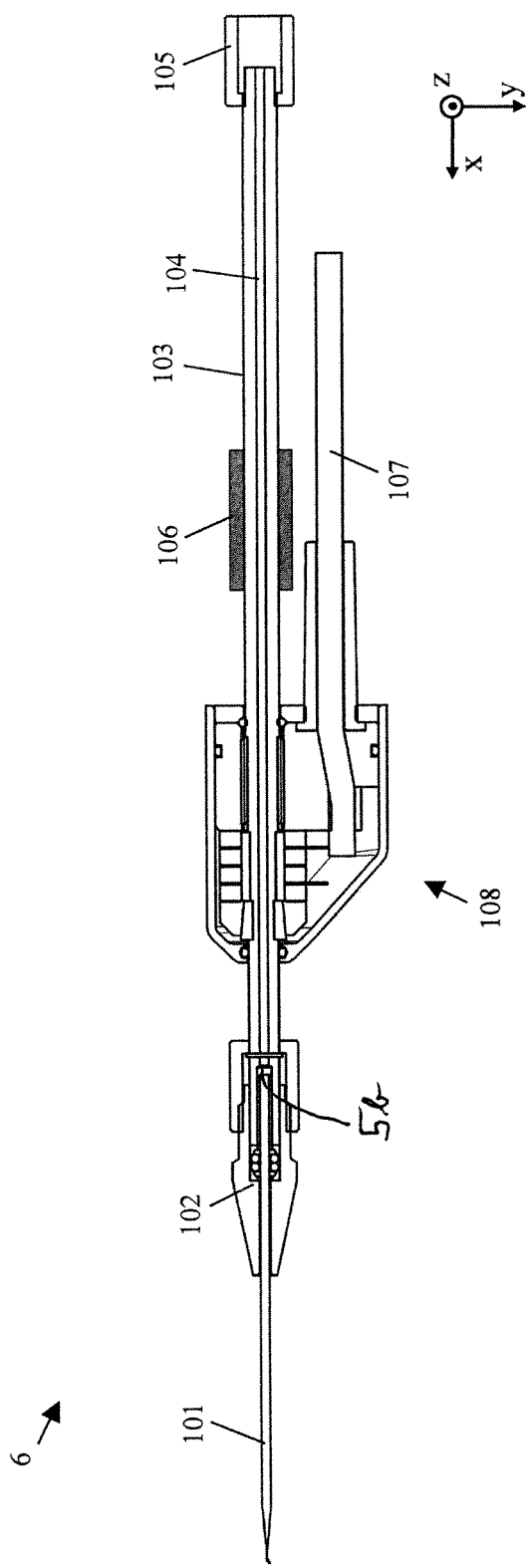
FIG. 3 shows a vertical cross section along the length of an embodiment of the apparatus according to the present invention.

FIG. 3 shows a vertical cross section along the length of an embodiment of the apparatus according to the present invention, which is the cell driller 6. The embodiment comprises the cell driller (apparatus for generating a tool motion) for the combination with a microinjector 11. The micro capillary 101 (tool) is hold by the mounting head 102, adapted as grip head. Alternative possible tools are microelectrodes or cutting tools for the use as microdissector, which is mounted to the motion section 5b of the actuated member 103. The channel of the micro capillary 101 is tightly connected by the assistance of sealing means to the channel 104 of the actuated member 103, which is adapted as capillary tube 103. The latter is connected via the junction 105 to the microinjector 11. Connecting means 106, e.g. a clamping device, are provided at the back part of the actuated member, i.e. the tube 103, to hold the cell driller 6. Control of the cell driller is performed via the power line 107, which connects the drive section 108 to the control device 9. During operation, the feed pipe 105 to the microinjector 11, the capillary tube 103 as well as a part of the micro capillary 101 are filled with silicon oil. The front part of the micro capillary 101 is usually filled with Fluorinert™ FC-77 or mercury. By pumping up or down liquid with the microinjector 11, the whole liquid column in the pipe system can be moved and thus, the uptake or release of liquid volume (and/or cell material) by the micro capillary 101 can be controlled.

Figure 4:
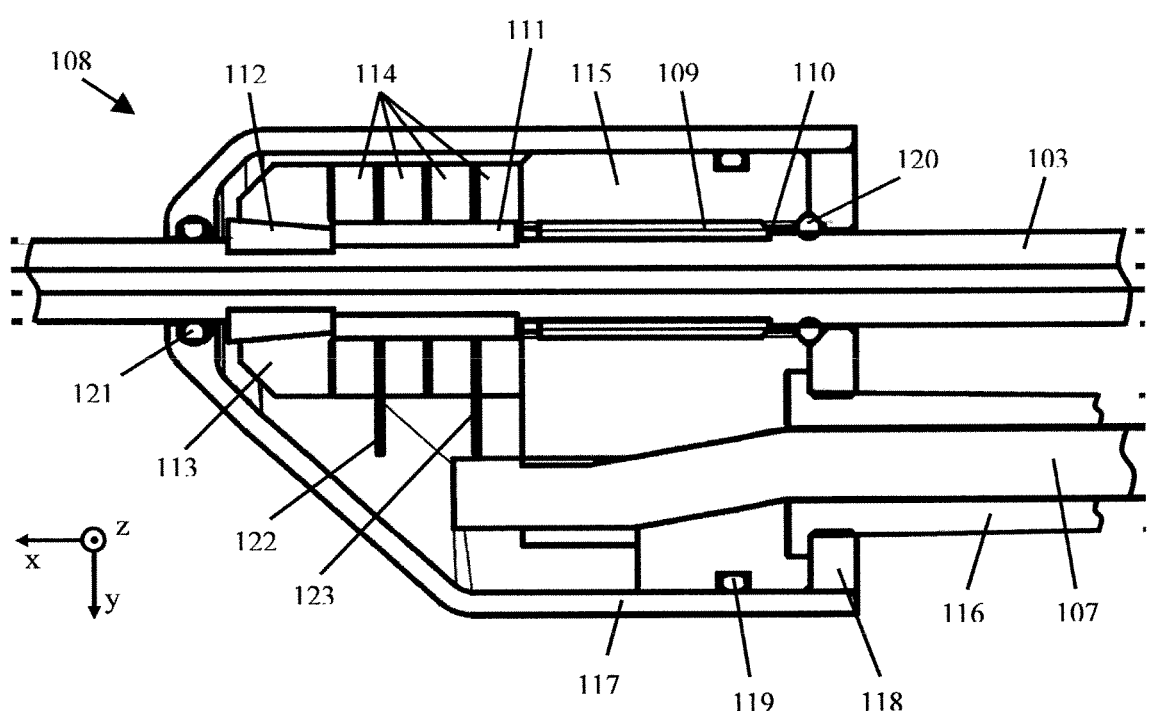
FIG. 4 shows details of the vertical cross section of FIG. 3.

FIG. 4 shows a detail picture of the drive section 108 of the vertical cross section of the cell driller 6 in FIG. 3. The assembly of the cell driller, in particular the assembly of the drive section 108 is explained. The drive section 108 seats on the tube 103, which is the carrier. First, a threaded sleeve 109 is slid on the tube, until it stops at a recess 110, which acts also as connecting means, where the force from the actuator element is transferred to the tube at the first position. Then, the insulating/center sleeve 111 is placed. A concentric groove is provided in the front of the tube 103, which serves as connecting means and which defines the second position, where the force from the actuator element is transferred to the tube 103, to expand the tube between said first and said second position upon actuation by the piezo elements. Into said groove, two cone-shaped ring-elements 112 are placed, which provide an increased outer diameter towards the front part of the cell driller, i.e. whose outer surface has a slope with an angle. Onto the cone-shaped ring-elements 112 is slid a cone-shaped disk 113, which has a slope of the same angle at its inner side, but in the opposite direction such that the parts 112 and 113 contact each other in a form-closure way. To the disk 113 are abutted the piezoelectric ring-elements 114, which are electrically insulated and centered against the tube 103 by the sleeve 111. Onto the threaded sleeve 109 the counter support 115 is screwed, until the piezo elements 114 are sufficiently under bias compression. Said compression is preferably chosen such that the piezo elements 114 during operation of the apparatus always stay under compression, preferably at least under said bias compression. This assures the safe mounting of the piezo elements 114 by clamping, such that an unintended shifting is avoided. Therefore, adhesive bonding or other connection of the piezo elements 114 is not required. Further, a tensile stress of the piezo elements can be avoided which can lead to a breach of the ceramics. The counter support 115 holds the power line 107 and the antikink 116.

The drive of the cell driller is enclosed by the housing 117 and the cover 118. Via the sealing rings 119, 120 and 121 the resulting interior space is sealed airtight and vapour-tight against the environment. Therefore, the piezo elements 114 are protected against dust and humidity.

In the following, the working principle of the cell driller 6 is explained referring to FIGS. 3 to 5. If an appropriate electric voltage is applied to the piezo elements 114 via the power line 107, the piezo elements expand in x-direction. However, they are clamped between a first and a second position, i.e. between the counter support 115 and the cone disk 113. These parts are hold by the threaded sleeve 109 and the ring-elements 112 respectively in relation to the direction of expansion of the tube firmly by the groove and the recess 110 of the tube, i.e. by the tube 103 itself. In principle, also a compression instead of an expansion of the tube can be utilized, which is not the case for the embodiment at hand.

The preferred material for the tube 103 is steel. As known, even steel is an elastically deformable material, which has a relatively high Young's Modulus (around 200 kN/mm² compared to silicon rubber with 0.05 kN/mm²). This means, steel can store much more energy in a predetermined volume than other material. On the other hand, much less compression distance is required to store a predetermined energy, if material with high Young's Modulus are used, as e.g. steel. For the amplitudes of motion required here, the expansion of steel can be performed easily by the actuator elements of the invention, in particular without breaking the tube 103 or plastically and irreversible deforming the steel. Steel further offers the advantage that the tube 103 gains a high mechanical stability.

As the ring-shaped piezo elements 114 are arranged coaxial to the tube 103, the resulting vector of force lies in the center of the crossection of the tube and points in the direction of the central axis (x-axis) of the tube. Therefore, no bending of the tube 103 is induced, but only expansion of the tube with subsequent elastic relaxation is effected. Due to the avoidance of bending, the deflection of the tip of the micro capillary 101 is prevented in the y- and z-direction, which keeps the bore-diameters and section-widths small.

Figure 5:
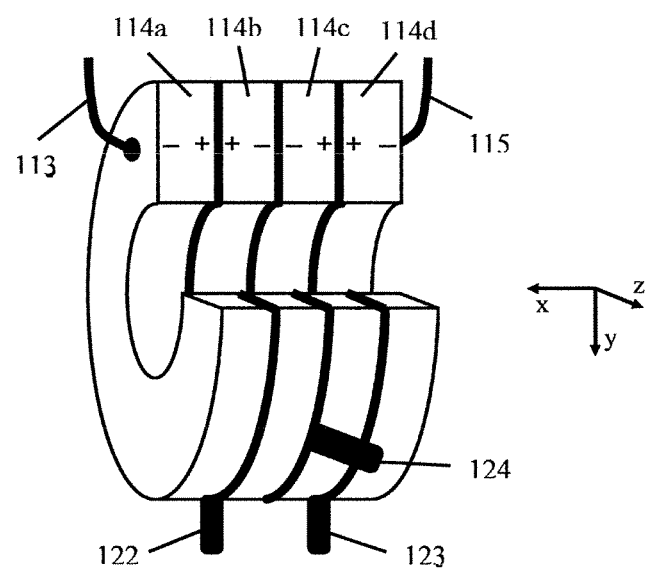
FIG. 5 shows an example for the arrangement and connection of an actuator element, which is a sequence of piezoelectric elements, which can be used for the apparatus of FIGS. 3 and 4.

FIG. 5 shows an example for the arrangement and connection of an actuator element, which is a sequence of piezoelectric elements, which can be used for the apparatus of FIGS. 3 and 4. Four circular-ring-shaped piezo elements 114a, 114 b, 114 c and 114d are used, which are poled to expand under voltage. The faces of the elements are provided with silver electrodes. Voltage is applied to the electrodes via ring-shaped metallic shim disks with extending contact plate 122, 123, 124. The contacts 122 and 123 are poled positive and are connected to the inner line of a coaxial cable, the contact 124 is poled negative and connected to the outer line of the cable. The back end of the stack of piezo elements 114 is negatively poled via the electric contact with the metallic counter support 115, wherein the counter support 115 is in contact with the outer line. The front end of the stack is also poled negative via the metallic cone disk 113, which is in electric contact with the cone-shaped ring-segments 112, the capillary tube 103, the metallic threaded hull 109 and the counter support 115.

The expansion of the piezo elements 114 is proportional to the applied voltage. Generally, the desired amplitude of motion of e.g. 2 μm could be achieved by using less than four piezo elements 114. Then, however, the required value for the voltage to be applied increases. For two piezo elements of the same type 114, the value is around 1000 V, for four elements it is at 500 V and for eight piezo elements 114 it is at 250 V. If more or far more than 500 V is required as operational power, then the costs for the required electronic components increase seriously. At 250 V the costs, which can be safed compared with 500 V-electronics, are negligible compared to the costs, which arise due to the additional number of piezo elements 114. Therefore, the preferred operation voltage for the cell driver 6 is between 300 V and 600 V and preferably at 500 V. However, as described, other values are also preferred. In particular, it has shown that the cell driller 6 can be operated sufficiently also with motion amplitudes of less than the discussed 2 μm, in particular at 1 μm or less, see the above examples for amplitudes.

The piezo elements 114 comprise crystals, whose electric field strength corresponds to the main direction of crystal deflection. Thus, they have to be contacted in the direction of expansion. This offers the advantage that the contacts can be provided on flat surfaces, namely the faces of the piezo elements 114. Otherwise, different type of piezo elements have to be contacted via their circumferential side, which is more costly, but can offer other advantages in certain configurations of the apparatus according to the present invention.

The invention claimed is:

1. An apparatus adapted to be used for In vitro fertilization, Intracytoplasmic sperm injection, Assisted Hatching, Enucleation, Nucleus transfers, Micro surgery, Patch Clamp or adapted for performing a single cell dissection from paraffin sections, a dissection of areas from histological sections and/or the Separation from stem cell aggregates from 3D-cell cultures, and for generating a motion of a tool for working on a biological cell material, the apparatus comprising:

at least one actuator element,
an actuated member, which is elastically deformable, and
a motion section, at which a tool can be arranged and which is linked to the actuated member, wherein the actuated member is an elongated part extending lengthwise along a central axis and wherein the at least one actuator element is linked at least at a first position and at a second position to the actuated member to act by a linear motion between said first position and said second position along a second axis, which is parallel or coaxial to the central axis, such that a motion of the motion section, which is caused by a length change of the actuated member upon actuation by the at least one actuator element, is linear and is coaxial or in parallel to said central axis, and wherein the at least one actuator element is connected at the first position and the second position to the actuated member, and the first position and the second position define a straight distance, which is parallel or coaxial with the central axis, the at least one actuator element being arranged to act along said straight distance to generate a linear motion of the at least one actuator element in parallel to said straight distance, the at least one actuator element being linked to the actuated member such that an actuation action by the at least one actuator element along a virtual axis elastically deforms the actuated member by a distance, which corresponds to a length change of the actuated member, wherein said length change causes said motion of the motion section and the amplitude of the motion equals to said length change at all times working on the biological cell material, a control device being provided for controlling the actuation by the at least one actuator element, the control device comprising electric circuitry and a microprocessor and being mounted to the apparatus or being arranged externally from the apparatus, the apparatus comprising input means for the user control of the apparatus, and the control device being adapted and programmed to generate a single motion of the motion section with at least a component along the central axis, wherein said single motion consists of one step of forth-motion, based on an increase of said distance, and one step of back-motion, based on a reduction of said distance, or the control device being adapted and programmed to generate a sequence of single motions of the motion section consisting of a predetermined number n of single motions with a frequency f, n being taken from the range 1 to 70 and f being a value of the range 1 to 40 Hz, the amplitude of the single motion being in the nanometer to micrometer range and being equal to or less than 2 µm.

2. The actuator apparatus according to claim 1, wherein the actuated member provides a first position and a second position, which are separated by a straight distance, which defines an axis, the actuator element being linked to the actuated member at least at said first position and at said second position, wherein upon actuation by the actuator element the actuated member undergoes a length change in the direction of said axis, wherein said length change corresponds to the distance of the elastic deformation of the actuated member between said first position and said second position.

3. The actuator apparatus according to claim 1 or 2, wherein the actuated member is made from an elastic material or comprises sections made from an elastic material.

4. The actuator apparatus according to claim 1, wherein the actuated member is made from an elastic material or comprises sections made from an elastic material, wherein said elastic material has a Young's Modulus of larger than 100 kN/mm², larger than 200 kN/mm², between 180 to 240 kN/mm² and/or where said elastic material is steel.

5. The actuator apparatus according to claim 1, wherein the at least one actuator element is arranged under a bias compression, preferably the bias compression chosen such that at no time of the operation of the apparatus the actuator element gets under tensile stress.

6. The actuator apparatus according to claim 1, wherein the actuated member extends along a central axis and the actuator element comprises at least one actuator member, in particular a piezoelectric element, which is arranged symmetrically in relation to said central axis.

7. The actuator apparatus according to claim 1, wherein the actuator element comprises at least one circular-ring-shaped actuator member.

8. The actuator apparatus according to claim 1, wherein the actuated member extends along a central axis, and wherein the motion section is arranged at the actuated member such that said axis extends through said motion section.

9. The actuator apparatus according to claim 1, wherein an inert mass element is provided and arranged in a force transfer chain between a first end of the at least one actuator element in relation to a direction of actuation, and a connecting means which is provided to mount the apparatus to a holder.

10. The actuator apparatus according to claim 1, wherein the actuated member is a bar part or a tubular part.

11. An actuator apparatus according to claim 1, wherein the predetermined number n of single motions is defined by a user via the input means.

12. An actuator apparatus according to claim 1, wherein the control device is adapted to perform the single motion or sequence of single motions after the user triggered the start of the performance of the single motion or sequence of single motions by way of the input means.

13. Actuator apparatus according to claim 1, wherein the control device being adapted and programmed to generate the sequence of single motions of the motion section consisting of the predetermined number n of single motions with a frequency f, f being a value of the range 1 to 10 Hz.

14. Actuator apparatus according to claim 1, wherein the actuated member is shaped cylindrically and the at least one actuator element has a ring-shaped structure and is arranged around the body of the actuated member.

15. A method for using the apparatus of claim 1 the method comprising the following steps:
actuating said actuated member by elastically deforming it, e.g. expanding or compressing it, by means of said at least one actuator element to induce a length change of the actuated member;
causing the motion of the motion section by said length change, wherein the amplitude of the motion equals to said length change at all times working on the biological cell material, the amplitude of the motion being in the nanometer to micrometer range and being equal to or less than 2 µm and the motion being a single motion of the motion section with at least a component along the central axis, wherein said single motion consists of one step of forth-motion, based on an increase of said distance, and one step of back-motion, based on a reduction of said distance or the motion being a sequence of single motions of the motion section consisting of a predetermined or user definable number n of single motions, n being taken from the range 1 to 70.

16. A process for drilling openings in biological cell membranes using the apparatus according to any one of claims 1-4, 5-8, and 9-10 comprising the following steps:
   connecting a tool to the motion section of said apparatus,
   actuating actuated member of said apparatus elastically deforming it, wherein said deforming comprises expanding or compressing it by means of said at least one actuator element to induce a length change of the actuated member;
   causing a motion of the motion section by said length change, wherein the amplitude of the motion equals to said length change, and wherein the
   tool connected to the motion section is linear moved forth and back to drill openings in biological cell membranes.

17. A process for cutting biological material using the apparatus according to any one of claims 1-4, 5-8 and 9-10 comprising the following steps:
   connecting a tool to the motion section of said apparatus,
   actuating actuated member of said apparatus by elastically deforming it, wherein said deforming comprises expanding or compressing it by means of said at least one actuator element to induce a length change of the actuated member;
   causing the motion of the motion section by said length change, wherein the amplitude of the motion equals to said length change, and the tool connected to the motion section is moved to cut biological material.

\* \* \* \* \*